United States Patent [19]

Kugler et al.

[11] 4,273,724

[45] Jun. 16, 1981

[54] HYDROCARBON SYNTHESIS FROM CO AND $H_2$ USING TITANIUM PROMOTED BULK NICKEL CATALYSTS

[75] Inventors: Edwin L. Kugler, Summit, N.J.; Robert L. Garten, Cupertino, Calif.

[73] Assignee: Exxon Research & Engineering Co., Florham Park, N.J.

[21] Appl. No.: 56,111

[22] Filed: Jul. 9, 1979

[51] Int. Cl.³ .................................................. C07C 1/04
[52] U.S. Cl. .................................... 518/715; 252/459; 252/455 R; 252/466 J; 252/472; 252/473; 252/474
[58] Field of Search ................. 260/449.6 R, 449.6 M

[56] References Cited

U.S. PATENT DOCUMENTS

| | | | |
|---|---|---|---|
| 2,244,196 | 6/1941 | Herbert | 260/449.6 R |
| 2,560,171 | 7/1951 | Hill | 260/449.6 R |
| 2,699,988 | 1/1955 | McGrath et al. | 260/449.6 R |
| 2,850,515 | 9/1958 | Riblett et al. | 260/449.6 R |
| 4,042,615 | 8/1977 | Vannice et al. | 260/449.6 R |

FOREIGN PATENT DOCUMENTS 465157  4/1937  United Kingdom ............... 260/449 M

*Primary Examiner*—Howard T. Mars
*Attorney, Agent, or Firm*—Joseph J. Allocca; Robert J. North

[57] ABSTRACT

Higher molecular weight hydrocarbons of from $C_2$ to $C_7$ carbon number are prepared from CO and $H_2$ by the method of passing the CO and $H_2$ at a ratio of from 10–0.1, a space velocity of from 100 $hr^{-1}$ to 50,000 $hr^{-1}$ over a bulk nickel catalyst promoted with from 0.001 to 25 wt. % titanium containing oxide (calculated as $TiO_2$), for a time sufficient to effect the generation of the desired hydrocarbon products, at a temperature of from 100° to 500° C. and a pressure of from 103 to $1.03 \times 10^5$ kPa. The hydrocarbon products obtained are clean, stable paraffin liquids. The activity of the instant process employing titanium promoted bulk nickel is from 3 to 5 times that of the process employing bulk nickel.

5 Claims, 2 Drawing Figures

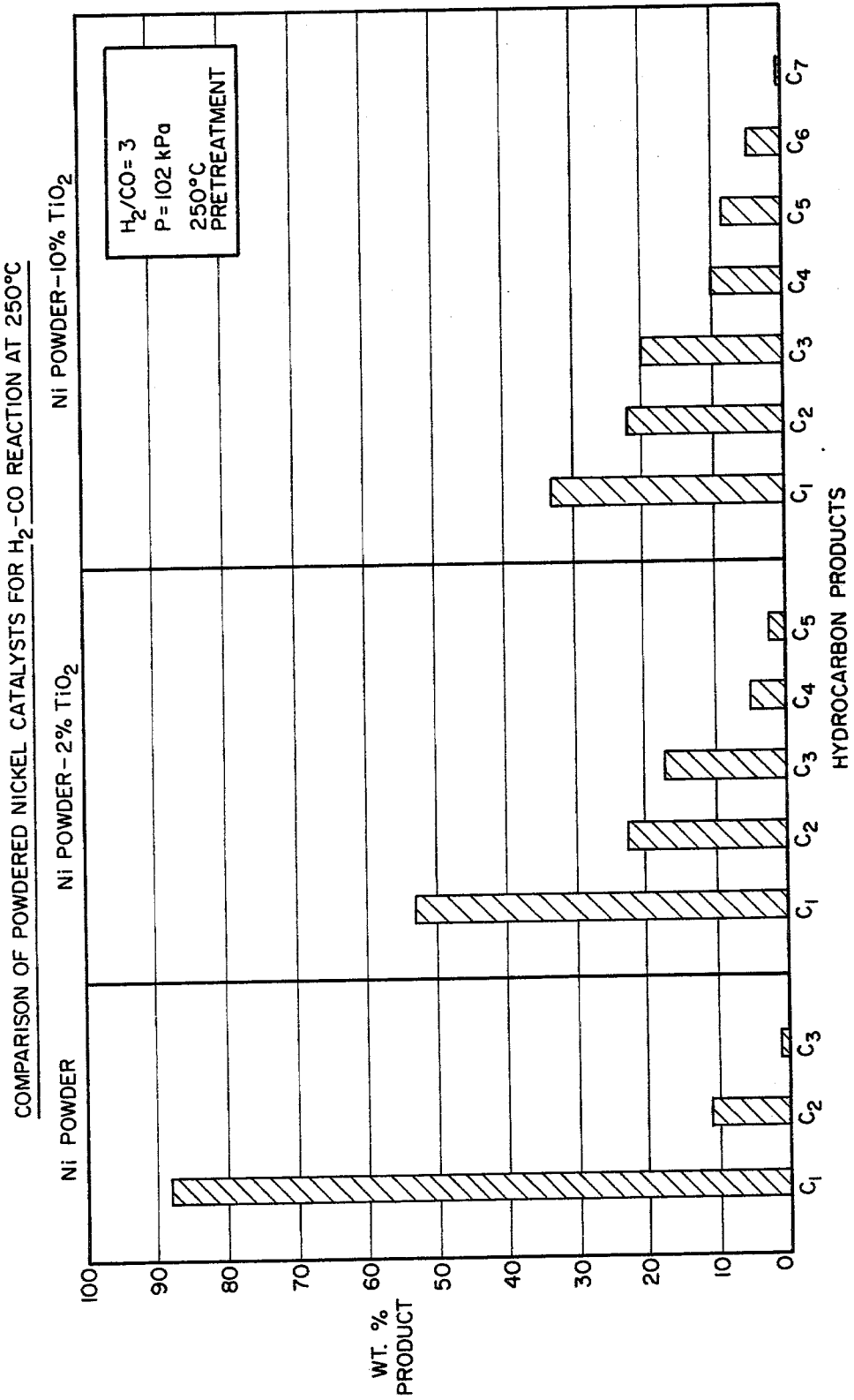

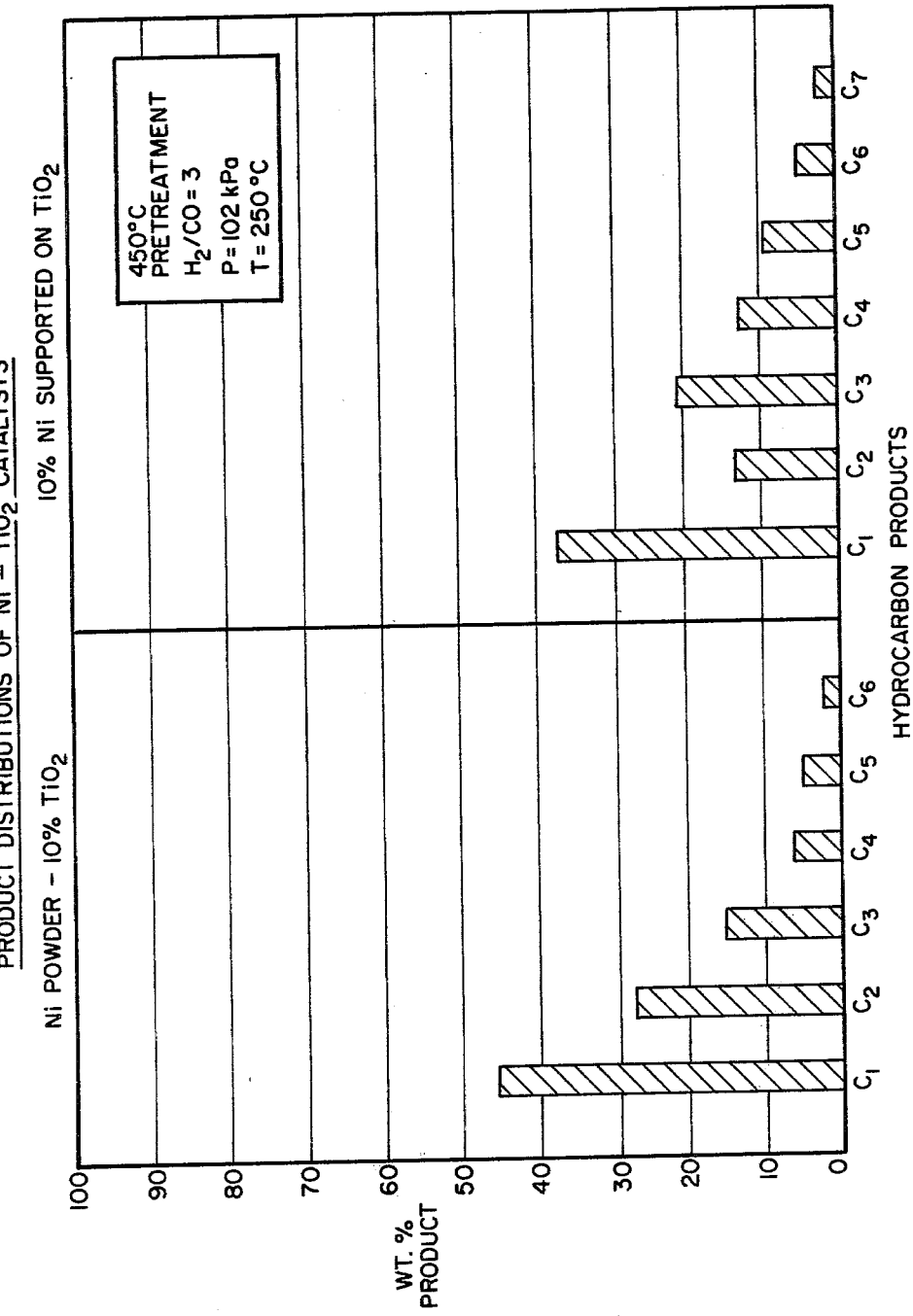

HYDROCARBON SYNTHESIS FROM CO AND $H_2$ USING TITANIUM PROMOTED BULK NICKEL CATALYSTS

PRIOR ART

Conventional state of the art nickel catalysts, i.e., $Ni/Al_2O_3$, $Ni/SiO_2$, Bulk Nickel, etc., are well-known for their selectivity toward methane formation, for example, see M. Greyson, "Catalysis," Vol. IV, 473 (1956) and H. A. Dirksen and H. R. Linden, Research Bulletin No. 31, Institute of Gas Technology (1963). Further work can be found in Shultz et al, Report of Investigations 6974, Bureau of Mines, 1967, Pages 1 through 18. All of these references disclose the amazing selectivity to methane exhibited by nickel and supported nickel catalysts. Within a wide range of temperature, pressure, and $H_2/CO$ ratios, methane is by far the predominant hydrocarbon product; and it is this fact that has made nickel the catalyst of choice for commercial methane synthesis from CO and $H_2$.

Recently, in U.S. Pat. No. 4,042,615 to Garten and Vannice, it has been revealed that nickel supported on $TiO_2$, other titanium-containing oxides, or mixtures thereof, wherein the nickel concentration ranges from 0.01 to 75 wt.%, preferably 1.5 to 10 wt.%, catalyzes the $CO/H_2$ reaction and results in the production of $C_2$ to $C_7$ paraffinic hydrocarbons at the expense of methane under fairly standard Fischer-Tropsch synthesis conditions. This effect, however, was observed only with the use of titanium oxides as supports. By way of contrast, the instant invention employs the nickel as the major component to which is added a relatively minor amount of titanium-containing oxide as a promoter.

G.B. Pat. No. 1,053,855 to Dent and Percival discloses a method for preparing a methane-containing gas which comprises passing a heated mixture of a hydrocarbon feedstock which is liquid at normal temperatures and pressures and boils below 300° C., from 0.1 to 2.5 lb. moles of hydrogen and at least 0.3 lb. moles of steam per pound atom of carbon in the feedstock, through a bed of highly active particulate solid metal catalyst under such conditions that the mixture reacts to produce substantially only products which are gaseous. The hydrogen charge may contain both hydrogen and CO and when the CO is present, it reacts with the $H_2$ to yield methane. The catalyst is preferably nickel promoted with a refractory oxide, for example, alumina, chromia or titania. Despite this teaching, however, the examples only employ nickel promoted with alumina. It is totally unexpected that nickel can be promoted with very low concentrations of titanium-containing oxides and that processes employing that catalyst yield paraffinic hydrocarbons of from 2 to 7 carbon atoms.

Another reference teaching nickel in combination with titania is U.S. Pat. No. 3,701,739; but in this reference, a broad combination of first and second metals are taught, and no specific reference or example is given for bulk nickel promoted with titanium oxide as a paraffinic hydrocarbon synthesis catalyst.

It has been discovered, and forms the basis of this disclosure, that the addition of titanium-containing oxides to bulk nickel metal, in the composition range of 0.001 to 25 wt.%, preferably 0.001 to 15 wt.%, more preferably 0.07 to 10 wt.%, most preferably 0.07 to 8.4 wt.% titanium oxide (calculated as $TiO_2$) to bulk nickel increases the activity of the bulk nickel and shifts the product spectrum to clean, stable paraffin liquids.

Higher molecular weight hydrocarbons of from $C_2$ to $C_7$ carbon number are prepared from CO and $H_2$ by the method of passing the syn gas at a $H_2/CO$ ratio of from 0.1 to 10, preferably 0.5 to 4, most preferably 1 to 3 at a space velocity of from 100 $hr^{-1}$ to 50,000 $hr^{-1}$ over a catalyst comprising bulk nickel promoted with from 0.001 to 25 wt.%, preferably 0.001 to 15 wt.%, more preferably 0.07 to 10 wt.%, most preferably 0.07 to 8.4 wt.% titanium-containing oxide (calculated as $TiO_2$) for a time sufficient to effect the generation of the desired paraffinic products at a temperature of from 100° to 500° C., preferably 150° to 400° C., most preferably 150° to 300° C. and a pressure of from $103-1.03 \times 10^5$ kPa, preferably 103–3090 kPa, most preferably 103–2060 kPa (1 atm. = 103 kPa).

The titanium-contantaining oxides, which are employed as promoters in the instant invention, are selected from the group consisting of $TiO_2$, $Al_2O_3$-$TiO_2$, $SiO_2$-$TiO_2$, $TiO_2$, $TiO_2$-carbon, $ZrTiO_4$, alkaline earth titanates ($BaTiO_3$, $CaTiO_3$, $SiTiO_3$, $MgTiO_3$), alkali titanates ($Na_2TiO_3$, $K_2TiO_3$, $Li_2TiO_3$) are rare earth titanates, preferably the titanium oxide is $TiO_2$.

The effect of titanium is to shift the product distribution towards higher molecular weight paraffins. Such a distribution of products could be highly desirable in a coal gasification-synthesis-electric power generation scheme where it is necessary to continuously run the coal gasifiers. In such an operation, it is desirable to be able to store a portion of the fuel from the CO—$H_2$ synthesis reactor for peak power demands. Such fuel must be stable to storage. The titanium promoted catalyst in the present invention holds promise for application in a coal gasification-synthesis-electric power generation scheme since a portion of the product is liquid paraffins which are stable and easily stored.

The titanium promoted nickel catalysts of the present invention would be employed in plate and grid assembly reactors where bulk nickel is sprayed or coated onto plates or grids used in reactor-heat exchanger devices. Examples of these types of devices are shown and discussed in the articles by W. P. Haynes, J. J. Elliott and A. J. Forney in *Am. Chem. Soc. Div. Fuel. Chem. Preprints*, Vol. 16(1), Page 44 (1972) and Vol. 16(2), Page 47 (1972).

Another application of the present invention is the modification of well-known Raney nickel catalysts. Raney nickel catalysts are porous bulk nickel of high surface area and high activity in hydrogenation and CO-$H_2$ synthesis reactions. Using the method described in the present invention, the activity of Raney nickel catalysts can be increased 3-fold by the addition of small amounts of titanium. The addition of titanium can also be employed to alter the product distribution of Raney nickel to favor production of clean, stable paraffin liquid fuels. Such titanium modified Raney nickel catalysts may also be employed in the plate and grid reactor-heat exchanger devices described above.

The catalysts employed in the instant process are prepared by techniques known in the art for the promotion of other catalyst systems. The bulk nickel metal is promoted by the addition of a solution of titanium oxide precursor—for example, titanium tert butoxide. The solvent may be any convenient solvent, but hydrocarbon solvents are preferred.

For all organo titanium compounds—for example, titanium tert-butoxide—nonaqueous solvents must be employed due to the sensitivity of organo titanium compounds to water. Preferably, the addition is from hydrocarbon solvent in a dry, inert atmosphere. The solvent is evaporated in the inert gas atmosphere, such as helium, nitrogen, argon, etc., leaving the titanium oxide precursor on the bulk nickel metal powder. The system is then subjected to air oxidation of the titanium oxide precursor on the nickel surface, which converts the precursor into titanium oxide. Finally, the system is reduced in a reducing atmosphere, typically hydrogen or any hydrogen-containing gas stream at a temperature sufficient to insure that the nickel is present as nickel metal. This procedure is necessary since, as will be seen, the mere physical admixture of $TiO_2$ to bulk nickel metal powder does not result in the desired promotional effect.

The nickel powder employed in the examples as such and as promoted is commercial Mond nickel powder. The chemical addition of titanium oxide to polycrystalline nickel powders changes the catalytic properties of the metal for hydrocarbon synthesis from carbon monoxide and hydrogen mixtures. Unless otherwise indicated, the catalysts of the examples were reduced for one hour at 250° C. in hydrogen mixtures. The influence of titanium oxide on catalytic selectivity is shown in Table 1 and for Ni powder, Ni powder 2% $TiO_2$ and Ni powder 10% $TiO_2$ in FIG. I.

The addition of titanium oxide to nickel reduced the methane concentration in the product and increased the proportion of higher molecular weight hydrocarbons. Similar selectivity patterns have been observed for catalysts with titanium oxide concentrations varying from 0.07 to 8.4%. The tendency toward heavier hydrocarbon products becomes more pronounced as the $TiO_2$ loading was increased.

TABLE 1

Selectivity of $TiO_2$ Promoted Nickel Catalysts

| | Temp. °C. | CO Conv. % | \multicolumn{7}{c}{Hydrocarbon Products (Wt. %)} |
|---|---|---|---|---|---|---|---|---|---|
| | | | $C_1$ | $C_2$ | $C_3$ | $C_4$ | $C_5$ | $C_6$ | $C_7$ |
| Ni Powder | 249.5 | 4.9 | 88 | 11 | 1 | — | — | — | — |
| 0.007% $TiO_2$ on Ni | 251.0 | 11.6 | 74 | 16 | 8 | 1 | trace | — | — |
| 0.07% $TiO_2$ on Ni | 248.5 | 27.2 | 38 | 19 | 23 | 9 | 7 | 3 | trace |
| 0.20% $TiO_2$ on Ni | 250.9 | 25.4 | 39 | 21 | 23 | 8 | 6 | 3 | trace |
| 1.66% $TiO_2$ on Ni | 250.8 | 15.9 | 36 | 23 | 21 | 10 | 7 | 4 | trace |
| 8.40% $TiO_2$ on Ni | 252.3 | 18.8 | 33 | 22 | 20 | 10 | 9 | 5 | trace |

P = 1 atm; $H_2/CO$ = 3

FIG. II displays the product distributions of a 10% Ni on $TiO_2$ catalyst and a Ni powder with a 10% $TiO_2$ promoter. Both samples had been reduced in flowing hydrogen for 1 hour at 450° C. Both catalysts produce hydrocarbons in the $C_1$ to $C_7$ range but there is a slight difference in the hydrocarbon products of the two catalysts. The 10% Ni/$TiO_2$ sample shows a maximum in the product distribution at $C_3$, whereas the Ni powder with 10% $TiO_2$ shows a smooth decrease in product concentration as the molecular weight increases.

An examination of the rates of hydrocarbon formation revealed that the change in selectivity pattern was not realized by suppressing the methanation rate but by enhancing the rate of higher hydrocarbon formation. Table 2 shows that the methanation rate increased when titanium oxide was added to a bulk nickel catalyst. However, the rate of carbon monoxide conversion increased more rapidly with the addition of promoter to account for the change in catalyst selectivity. The titanium oxide additative enhanced the methanation rate by as much as two-fold and the carbon monoxide conversion rate by as much as six-fold.

TABLE 2

Activity of $TiO_2$ Promoted Nickel Catalysts

| | Temp. °C. | Methanation Rate $\mu$moles/min/g of Ni | CO Conversion Rate $\mu$moles/min/g of Ni |
|---|---|---|---|
| Ni Powder | 249.5 | 9.7 | 11.0 |
| 0.007% $TiO_2$ on Ni | 251.0 | 19.1 | 26.3 |
| 0.07% $TiO_2$ on Ni | 248.5 | 21.9 | 60.2 |
| 0.20% $TiO_2$ on Ni | 250.9 | 21.2 | 56.6 |
| 1.66% $TiO_2$ on Ni | 250.8 | 11.7 | 34.7 |
| 8.40% $TiO_2$ on Ni | 252.3 | 14.3 | 46.0 |

P = 1 atm; $H_2/CO$ = 3

The improved activity and selectivity of titanium oxide promoted nickel catalysts is similar to that of nickel supported on titanium oxide. Tables 3 and 4 compare the catalytic properties of titanium promoted and titanium supported nickel. Both catalysts have similar product distributions. Both catalysts also have comparable activities when hydrogen chemisorption is used to estimate the number of nickel atoms on the catalyst surface. These similarities suggest that the mode of catalytic enhancement of nickel activity is the same for both materials.

A physical mixture of nickel and titanium oxide powders was prepared by stirring the two components together to test for a synergistic interaction that might occur on catalysts activation. None was observed. The physical mixture had the catalytic properties of nickel powder alone. The lack of modified catalytic properties with a physical mixture shows that a chemical interaction between nickel and titanium oxide is necessary to change the activity and selectivity of the metal catalyst.

Evidence for a chemical interaction between nickel and titanium oxide with promoted bulk nickel catalysts has been obtained by electron spectroscopy. ESCA results reveal that titanium exists on the nickel surface prior to reduction as $Ti^{4+}$, the oxidation state expected for a $TiO_2$ layer. After reduction in hydrogen at 250° C., some of the $Ti^{4+}$ is reduced to a lower oxidation state, but is not reduced to metallic titanium. The partial reduction of the titaium oxide surface layer indicates a chemical interaction between the nickel and titanium.

TABLE 3

Selectivity of Nickel-Titanium Oxide Catalysts

| | Temp. °C. | CO Conv. % | $C_1$ | $C_2$ | $C_3$ | $C_4$ | $C_5$ | $C_6$ | $C_7$ |
|---|---|---|---|---|---|---|---|---|---|
| 10% Ni on $TiO_2$ | 250.3 | 49.0 | 37 | 13 | 21 | 12 | 9 | 5 | 2 |

TABLE 3-continued

Selectivity of Nickel-Titanium Oxide Catalysts

| | Temp. °C. | CO Conv. % | Hydrocarbon Products (Wt. %) | | | | | | |
|---|---|---|---|---|---|---|---|---|---|
| | | | $C_1$ | $C_2$ | $C_3$ | $C_4$ | $C_5$ | $C_6$ | $C_7$ |
| 0.20% $TiO_2$ on Ni Powder | 250.9 | 25.4 | 39 | 21 | 23 | 8 | 6 | 3 | trace |
| 1:1 mixture of Ni Powder + $TiO_2$ | 252.0 | 2.1 | 92 | 8 | trace | — | — | — | — |
| Ni Powder | 249.5 | 5.1 | 88 | 11 | 1 | — | — | — | — |

P = 1 atm; $H_2/CO = 3$

TABLE 4

Activity of Nickel-Titanium Oxide Catalysts

| | Temp. °C. | Methanation Rate reactions/site/sec | CO Conversion Rate reactions/site/sec |
|---|---|---|---|
| 10% Ni on $TiO_2$ | 250.3 | 0.0194 | 0.0550 |
| 0.20% $TiO_2$ on Ni Powder | 250.9 | 0.0281 | 0.0748 |
| 1:1 mixture of Ni Powder + $TiO_2$ | 252.0 | 0.0101 | 0.0110 |
| Ni Powder | 249.5 | 0.0115 | 0.0131 |

P = 1 atm; $H_2/CO = 3$

The titanium promoter changes the surface area and chemisorption properties of bulk nickel. Table 5 shows the effect of titanium loading on the BET surface area and hydrogen chemisorption capacity for a series of samples. Small quantities of titanium additive increased the total surface area of the nickel powder. This increase shows that titanium promoters produce a rough surface coating, indicative of an oxide layer. The presence of this oxide layer was confirmed by the ESCA results. The titanium promoter also lowered the hydrogen chemisorption capacity of the nickel powder. It seems likely that the quantity of hydrogen chemisorption was reduced by titanium oxide physically blocking sites that would normally adsorb hydrogen.

If hydrogen chemisorption is used as a measure of reaction site population, the specific activity (turnover number) for the catalyst series may be calculated. This data is presented in Table 6. The specific activity reached a maximum value with the 0.07% $TiO_2$ sample. The overall activity was also maximized with this same sample.

TABLE 5

Chemisorption Properties of Promoted Nickel Powders

| | $H_2$ Chemisorption (μmoles/g) | BET Surface Area ($m^2/g$) | H/M |
|---|---|---|---|
| Ni powder | 7.0 | 0.41 | 0.00082 |
| 0.007% $TiO_2$ on Ni | 5.4 | 0.48 | 0.00063 |
| 0.07% $TiO_2$ on Ni | 3.9 | 0.60 | 0.00046 |
| 0.20% $TiO_2$ on Ni | 6.4 | 1.15 | 0.00075 |
| 1.66% $TiO_2$ on Ni | 4.0 | 7.69 | 0.00047 |

TABLE 6

Specific Activity of Promoted Nickel Powders

| | Temp. °C. | Turnover Number (reactions/site/sec.) | |
|---|---|---|---|
| | | Methane Formation | CO Conversion Rate |
| Ni Powder | 249.5 | 0.0115 | 0.0131 |
| 0.007% $TiO_2$ on Ni | 251.0 | 0.0295 | 0.0406 |
| 0.07% $TiO_2$ on Ni | 248.5 | 0.0468 | 0.129 |

TABLE 6-continued

Specific Activity of Promoted Nickel Powders

| | Temp. °C. | Turnover Number (reactions/site/sec.) | |
|---|---|---|---|
| | | Methane Formation | CO Conversion Rate |
| 0.20% $TiO_2$ on Ni | 250.9 | 0.0281 | 0.0748 |
| 1.66% $TiO_2$ on Ni | 250.8 | 0.0244 | 0.0723 |

P = 1 atm; $H_2/CO = 3$

A standard sample of nickel powder with 1.6% Ti (computed as $TiO_2$) was prepared and characterized by chemisorption, scanning electron microscopy and kinetic behavior for hydrocarbon synthesis from $H_2$ and CO. Similar measurements on the starting material (Mond nickel powder) were compared with this data to obtain information on the physical and chemical changes that occurred when titanium oxide was added to the nickel powder.

The Mond nickel powder had a surface area of 0.41 $m^2/g$ as determined by the BET method using argon (13.7 $A^2$/molecule). After this powder had been reduced in flowing hydrogen at 250° C., the same value of 0.41 $m^2/g$ was determined indicating that the mild reduction conditions employed had no significant effect on the size of the metal particles. Hydrogen chemisorption measurement provided a value for the surface density of nickel atoms of $2.05 \times 10^{19}$ atoms/$m^2$. This is in reasonable agreement with the value of $1.54 \times 10^{19}$ atoms/$m^2$ provided by Anderson for the polycrystalline nickel foil.

The addition of 1.66% titanium oxide to the nickel powder caused the surface area of the sample to increase to 7.69 $m^2/g$. If the titanium oxide were forming a smooth coating on the surface of the nickel powder, the diameter of the particles would increase and the surface area per gram of sample would show no significant change. The large increase in surface area that accompanied a necessary increase in particle size indicates that a rough surface coating of titanium oxide must have formed. Hydrogen chemisorption measurements confirmed this roughness, for only 40% of the surface nickel atoms were blocked by the titanium oxide whereas all of the surface nickel atoms would have been blocked if a uniform coating were to form over the metal particles.

The adsorption data for both powdered nickel samples are summarized in Table 5.

The powdered nickel sample with 1.6% Ti that had previously been used for adsorption measurements was examined in the scanning electron microscope. The sample appeared to consist of a number of spheres cemented together to form chains. The size of the spheres varied from 1.0 to 2.4μ. If the nickel powder used to prepare this sample had consisted of uniform spheres, a particle diameter of 1.6μ would have the experimentally measured surface area of 0.41 m²/g. The scanning electron microscope also showed small crystallites of 0.1-0.4μ on the surface of the larger spheres so that the particles had a rough, uneven appearance. Hence, it appears that the addition of titanium to the nickel powder produced small titanium oxide crystallites on the metal surface. This observation is in full agreement with the surface area and hydrogen chemisorption measurements obtained for this sample.

What is claimed is:

1. A process for the synthesis of higher molecular weight paraffinic hydrocarbons of from $C_2$ to $C_7$ carbon number comprising the steps of passing CO and $H_2$ at a CO/$H_2$ ratio of from 10 to 0.1, at a space velocity of from 100 hr$^{-1}$ to 50,000 hr$^{-1}$, at a temperature of from 100° to 500° C. and at pressures of from 103 to $1.03 \times 10^5$ kPa over a catalyst comprising bulk nickel promoted with from 0.07 to 10 wt.% titanium containing oxide (calculated as $TiO_2$) for a time sufficient to effect the generation of the desired paraffinic products.

2. A method of claim 1 wherein the titanium containing oxide is $TiO_2$, $Al_2O_3$-$TiO_2$, $SiO_2$-$TiO_2$, $TiO_2$-carbon, $ZrTiO_4$, alkaline earth titanates, alkali titanates and rare earth titanates.

3. The method of claim 1 wherein the titanium containing oxide is $TiO_2$.

4. The method of claim 1, 2 or 3 wherein the $H_2$/CO ratio is from 0.5 to 4, the temperature is from 150° to 400° C. and the pressure is from 103 to 3090 kPa.

5. The method of claim 1, 2 or 3 wherein the $H_2$/CO ratio is from 1 to 3, the temperature is from 150° to 300° C. and the pressure is from 103 to 2060 kPa.

* * * * *